United States Patent
Urano

(10) Patent No.: US 9,829,454 B2
(45) Date of Patent: Nov. 28, 2017

(54) COIL UNIT AND APPARATUS FOR DETECTING FOREIGN MATTER

(71) Applicant: TDK CORPORATION, Tokyo (JP)

(72) Inventor: Takashi Urano, Tokyo (JP)

(73) Assignee: TDK CORPORATION, Tokyo (JP)

( * ) Notice: Subject to any disclaimer, the term of this patent is extended or adjusted under 35 U.S.C. 154(b) by 217 days.

(21) Appl. No.: 14/554,967

(22) Filed: Nov. 26, 2014

(65) Prior Publication Data

US 2015/0145530 A1  May 28, 2015

(30) Foreign Application Priority Data

Nov. 28, 2013  (JP) ................. 2013-246452
Oct. 3, 2014  (JP) ................. 2014-204703

(51) Int. Cl.
*G01R 27/26*  (2006.01)
*G01N 27/02*  (2006.01)
(Continued)

(52) U.S. Cl.
CPC ......... *G01N 27/025* (2013.01); *H01F 27/402* (2013.01); *H01F 38/14* (2013.01); *H02J 5/005* (2013.01); *G01V 3/105* (2013.01)

(58) Field of Classification Search
CPC .... G01R 27/02; G01R 27/2611; G01V 3/101; B60R 21/015
(Continued)

(56) References Cited

U.S. PATENT DOCUMENTS 7,952,365 B2 * 5/2011 Narita .................. H05K 1/0268
324/633
8,638,178 B1 * 1/2014 Wang .................. H03H 3/0075
310/344
(Continued)

FOREIGN PATENT DOCUMENTS

JP  2012-16125 A  1/2012
JP  2013-099090 A  5/2013
(Continued)

OTHER PUBLICATIONS

May 6, 2015 Search Report issued in European Application No. 14195246.5.
(Continued)

*Primary Examiner* — Tung X Nguyen
*Assistant Examiner* — Dominic Hawkins
(74) *Attorney, Agent, or Firm* — Oliff PLC

(57) ABSTRACT

The present invention aims to provide a coil unit for improving an accuracy in detecting foreign matter and an apparatus for detecting foreign matter which improves the accuracy in detecting foreign matter when a power is transmitted in a contactless manner. A power feeding coil unit (a coil unit) of the present invention is provided with a power feeding coil (a coil for power transmission) and an apparatus for detecting foreign matter. The apparatus for detecting foreign matter is provided with a plurality of resonators having a resonator coil and a resonator capacitor and also an excitation coil for exciting the plurality of resonators. The plurality of resonators are disposed to cover at least an area interlinking with a magnetic flux generated by the power feeding coil and to decrease an influence of mutual inductance.

7 Claims, 8 Drawing Sheets

(51) Int. Cl.
*H02J 5/00* (2016.01)
*H01F 27/40* (2006.01)
*H01F 38/14* (2006.01)
*G01V 3/10* (2006.01)

(58) Field of Classification Search
USPC ....... 324/655, 654, 633, 652, 668, 656, 606, 324/647, 665, 672, 705
See application file for complete search history.

(56) References Cited

U.S. PATENT DOCUMENTS

| | | | | |
|---|---|---|---|---|
| 9,465,064 | B2* | 10/2016 | Roy | G01V 3/081 |
| 2009/0278552 | A1* | 11/2009 | Jakkula | G01B 15/02 |
| | | | | 324/633 |
| 2012/0326523 | A1 | 12/2012 | Fukushima | |
| 2013/0094598 | A1* | 4/2013 | Bastami | H02J 5/005 |
| | | | | 375/259 |
| 2013/0099592 | A1 | 4/2013 | Abe | |
| 2013/0229241 | A1* | 9/2013 | Imamura | H03H 7/09 |
| | | | | 333/185 |
| 2013/0241302 | A1* | 9/2013 | Miyamoto | G01N 27/00 |
| | | | | 307/104 |
| 2013/0257168 | A1* | 10/2013 | Singh | H02J 17/00 |
| | | | | 307/104 |
| 2014/0015329 | A1 | 1/2014 | Widmer et al. | |
| 2014/0084857 | A1* | 3/2014 | Liu | H02J 5/005 |
| | | | | 320/108 |

FOREIGN PATENT DOCUMENTS

| | | |
|---|---|---|
| JP | 2013-192390 A | 9/2013 |
| WO | 2014/011788 A1 | 1/2014 |
| WO | 2014/095722 A2 | 6/2014 |

OTHER PUBLICATIONS

U.S. Appl. No. 14/554,811, filed Nov. 26, 2014 in the name of Urano.
May 4, 2015 Search Report issued in European Patent Application No. 14195201.0.
Application No. 14/554,967 filed Nov. 26, 2014 in the name of Urano.
Apr. 3, 2017 Office Action issued in U.S. Appl. No. 14/554,811.
Sep. 6, 2017 Office Action Issued in U.S. Appl. No. 14/554,811.

* cited by examiner

COIL UNIT AND APPARATUS FOR DETECTING FOREIGN MATTER

The present invention relates to a coil unit and an apparatus for detecting foreign matter.

BACKGROUND

The contactless power transmission in which the power is supplied without using a power cord is attracting attentions. The conventional contactless power transmission is mainly the type based on the electromagnetic induction. It is expected that this technique can be applied to various fields.

In view of the circumstance shown above, such a project is being studied that an electric vehicle is provided with a power receiving coil at its bottom part (power receiving side) and a high power (for example, several kilowatt to several tens of kilowatt) is transmitted in a contactless manner from a power feeding coil on the ground (power feeding side). If the contactless power transmission can be utilized, then the power can be transmitted without mechanically coupling power feeding side to power receiving side.

However, if some foreign matter are present in the gap between the power feeding coil and the power receiving coil when the power is being transmitted in a contactless manner, concerns rise that when the foreign matter is a metal, an eddy current will generate due to the magnetic flux passing through the foreign metal. If the foreign matter is a magnetic body, there will be a hysteresis loss due to the magnetic flux passing through the foreign magnetic body, so that the foreign matter may be heated.

As a way to avoid the heating problem, Patent Document 1 has suggested a detecting apparatus with a detecting part. Specifically, the detecting part is provided with one or a plurality of magnetic coupling elements which is/are composed of a plurality of coils. It measures the electric parameters related to the magnetic coupling element(s) or a circuit containing at least the magnetic coupling element(s) and then determines whether a foreign matter that may generate heat due to the magnetic flux is present based on the changes of these electric parameters.

PATENT DOCUMENT

Patent Document 1: JP-A-2013-192390

SUMMARY

However, with respect to the technique disclosed in Patent Document 1, a plurality of detecting coils (magnetic coupling elements) are disposed without gaps to eliminate the dead area where the foreign metal cannot be detected, wherein the plurality of detecting coils are connected to the capacitor for resonance and resonates with a given frequency. In this respect, several resonance frequencies are present for each detecting coil (magnetic coupling element) so that the measurement becomes difficult. Further, the Q value of each detecting coil is significantly lowered and the measuring accuracy becomes worse. Thus, a problem is there that the accuracy in detecting the foreign metal is deteriorated.

Therefore, the present invention is provided in view of the related problems. The present invention aims to provide a coil unit with a better accuracy in detecting foreign matter and an apparatus for detecting foreign matter with a better accuracy in detecting foreign matter when the power is transmitted in a contactless manner.

The coil unit of the present invention is characterized in that it is a coil unit used for contactless power transmission from power feeding side to power receiving side. The coil unit is provided with a coil for power transmission and an apparatus for detecting foreign matter. The apparatus for detecting foreign matter is provided with a plurality of resonators having a resonance coil and a resonance capacitor and also an excitation coil which excites the plurality of resonators. The plurality of resonators are disposed so as to cover at least an area interlinking with a magnetic flux generated by the coil for power transmission and to decrease the influence of mutual inductance.

In the present invention, the plurality of resonators are disposed so as to cover at least the area interlinking with the magnetic flux generated by the coil for power transmission and to decrease the influence of mutual inductance. Thus, even if the plurality of resonators are disposed without gaps in an area for metal detection, each resonator can be prevented from influencing each other. In this respect, each resonator is prevented from generating multiple resonance frequencies so that a decrease of Q value will be inhibited. As a result, the accuracy in detecting metals will be improved when power is transmitted in a contactless manner.

The coil unit of the present invention is characterized in that it is a coil unit used for contactless power transmission from power feeding side to power receiving side. The coil unit is provided with a coil for power transmission and an apparatus for detecting foreign matter. The apparatus for detecting foreign matter is provided with a plurality of resonators having a resonance coil and a resonance capacitor and also an excitation coil which excites the plurality of resonators. The plurality of resonators are disposed to cover at least an area interlinking with a magnetic flux generated by the coil for power transmission. In addition, the plurality of resonators disposed to be adjacent with each other in a row direction and a column direction are disposed in layers so that the plurality of resonators do not overlap with each other when viewed in a direction perpendicular to a surface and the distances from the resonators to the excitation coil are different from each other.

In the present invention, the plurality of resonators are disposed in rows and columns so as to at least cover the area interlinking with the magnetic flux generated by the coil for power transmission, and the plurality of resonators disposed to be adjacent in the row direction and the column direction are disposed in layers so that the plurality of resonators do not overlap with each other when viewed in a direction perpendicular to the surface and the distance from the resonators to the excitation coil is different from each other. Thus, even if the plurality of resonators are disposed without gaps in an area for metal detection, each resonator can be prevented from influencing each other. In this respect, each resonator is prevented from generating multiple resonance frequencies so that a decrease of Q value will be inhibited. As a result, the accuracy in detecting foreign matter will be improved when power is transmitted in a contactless manner.

It is preferable that in the plurality of resonators disposed adjacent with each other in the column direction and the row direction, an axis of the resonance coil in each resonator inclines in a direction opposite to each other with respect to an axis of the excitation coil. As such, even if the plurality of resonators are disposed without gaps in an area for metal detection, each resonator can be further prevented from influencing each other. In this respect, each resonator is prevented from generating multiple resonance frequencies so that a decrease of Q value will be further inhibited. As a result, the accuracy in detecting foreign matter will be further improved when power is transmitted in a contactless manner.

Preferably, the apparatus for detecting foreign matter is further provided with a plurality of detecting coils and each of the plurality of detecting coils is disposed so as to be magnetically coupled to each resonator of the plurality of resonators. As such, since the Q values of the plurality of resonators can be indirectly measured without connecting a means for Q value measurement directly to the plurality of resonators, the Q values of the plurality of resonators can be further prevented from decreasing without changing the resonance frequencies of the plurality of resonators.

The apparatus for detecting foreign matter is characterized in that it is an apparatus for detecting foreign matter for a detection of foreign matter and is provided with a plurality of resonators having a resonance coil and a resonance capacitor and also an excitation coil which excites the plurality of resonators. The plurality of resonators are placed in rows and columns in an in-plane direction, and the plurality of resonators disposed adjacent with each other in a column direction or a row direction are disposed in layers so that the plurality of resonators do not overlap with each other when viewed in a direction perpendicular to a surface and the distance from the resonators to the excitation coil are different from each other.

In the present invention, the plurality of resonators are placed in rows and columns in the in-plane direction, and the plurality of resonators disposed to be adjacent in the column direction or the row direction are disposed in layers so that the plurality of resonators do not overlap when viewed in a direction perpendicular to the surface and the distance from the resonators to the excitation coil are different from each other. Thus, even if the plurality of resonators are disposed without gaps in an area for metal detection, each resonator can be prevented from influencing each other. In this respect, each resonator is prevented from generating multiple resonance frequencies so that a decrease of Q value will be inhibited. As a result, the accuracy in detecting foreign matter can be improved.

In the present invention, what can be provided is a coil unit with an improved accuracy in detecting foreign matter and an apparatus for detecting foreign matter with an improved accuracy in detecting foreign matter when power is transmitted in a contactless manner.

DETAILED DESCRIPTION OF EMBODIMENTS

Figure 1:
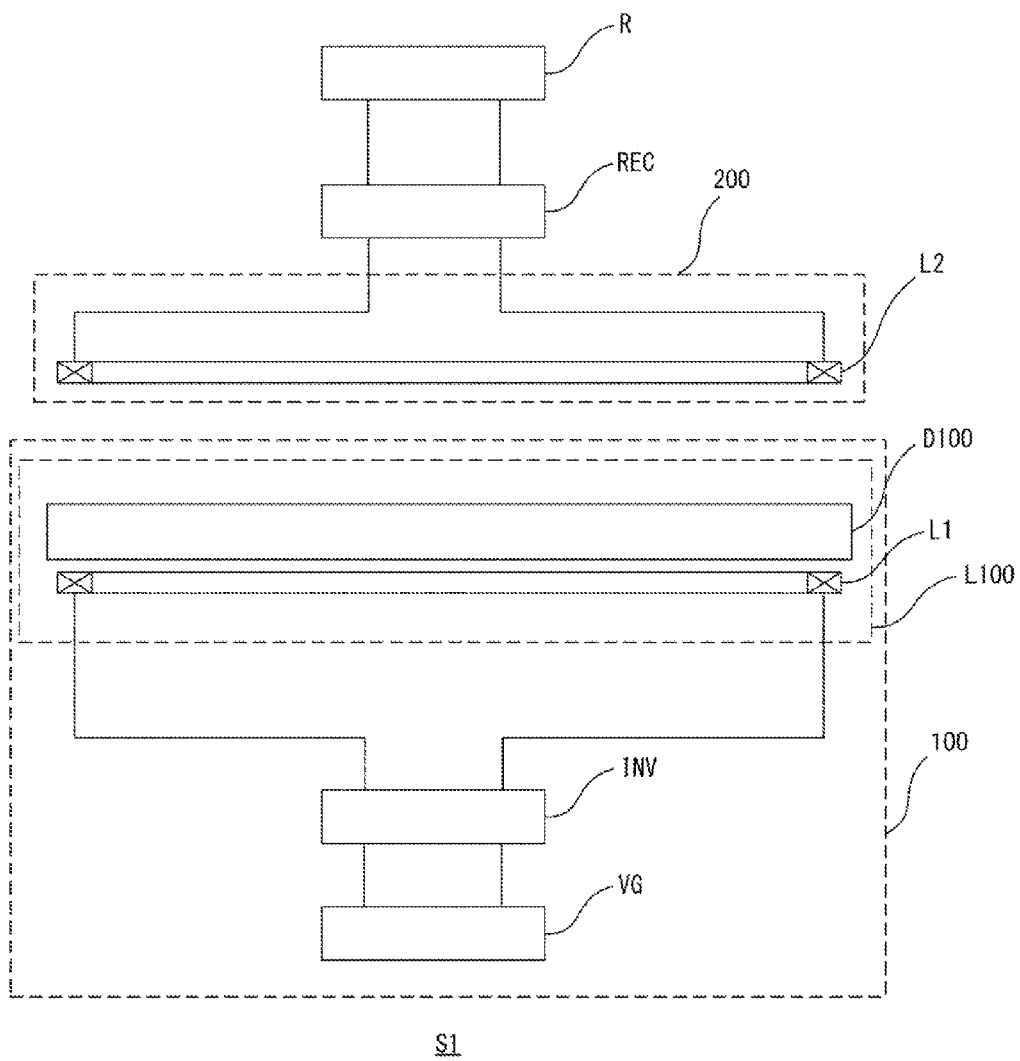
FIG. 1 is a schematic view showing the apparatus, to which the coil unit of the present invention is applied, for contactless power transmission together with a load.

The embodiments for carrying out the present invention will be described in detail with reference to the drawings. However, the present invention is not limited to the following embodiments. Further, the constituent elements described below contain those easily thought of by one skilled in the art and those substantially the same. In addition, the same reference numeral refers to the same element or an element having the same function, and repeated descriptions will be omitted.

First of all, the overall structure of the apparatus S1 for contactless power transmission to which the coil unit of the preferable embodiments is applicable will be described with reference to FIG. 1 before the coil unit of the preferable embodiments in the present invention. FIG. 1 is a schematic view showing the apparatus, to which the coil unit of the preferable embodiments is applied, for contactless power transmission together with the load. In addition, the coil unit of the present invention can be used as any one of a power feeding coil unit in a power feeding apparatus and a power receiving coil unit in a power receiving apparatus. However, in the following embodiments, the coil unit of the present invention will be described in examples in which the coil unit is applied as the power feeding coil unit in a power feeding apparatus.

As shown in FIG. 1, the apparatus S1 for contactless power transmission is provided with a power feeding apparatus 100 and a power receiving apparatus 200. Here, the apparatus S1 for contactless power transmission is described in an example in which the apparatus S1 is used as a power feeding apparatus for supplying power to a moving object such as an electric vehicle.

The power feeding apparatus 100 is provided with a voltage source VG, a power conversion circuit INV and a power feeding coil unit L100. The voltage source VG feeds a direct current to the power conversion circuit INV described later. The voltage source VG is not particularly restricted as long as it outputs a direct current. For example, the power supply can be a direct-current power supply from a rectified and stabilized commercial alternating-current power supply, a secondary battery, a direct-current power supply with power generated via solar energy, or a switching power supply such a switching converter.

The power conversion circuit INV converts the direct current supplied from the voltage source VG to an alternating current and then supplies the alternating voltage to the power feeding coil unit L100 described later. In other words, the power conversion circuit INV functions as an inverter. In addition, the power conversion circuit INV can be composed of, for example, a switching circuit with multiple switching elements being bridge connected (not shown in the figures). The switching element forming the switching circuit can be, for example, an element such as MOS-FET (metal oxide semiconductor-field effect transistor), IBGT (insulated gate bipolar transistor) or the like.

The power feeding coil unit L100 functions as a power supplying part for transmitting the alternating current in a contactless manner to the power receiving apparatus 200, which is to be described later. The power feeding coil unit L100 is disposed below the ground or at somewhere near the ground. Further, the specific structure of the power feeding coil unit L100 will be described later.

The power receiving apparatus 200 is provided with a power receiving coil L2 and a rectification circuit REC. As in the present embodiment, when the apparatus S1 for contactless power transmission is applicable to a power feeding apparatus for supplying power to a moving object such as an electric vehicle, the power receiving apparatus 200 is provided on the moving object. Here, the moving object provided with the power receiving apparatus 200 can be an electric vehicle or a hybrid vehicle utilizing the power from a secondary battery.

The power receiving coil L2 functions as a power receiving part for receiving the alternating power supplied from the power feeding coil unit L100 in a contactless manner. The power receiving coil L12 is disposed at the bottom part of the electric vehicle.

The rectification circuit REC rectifies the alternating current received by the power receiving coil L2 to a direct current and then outputs the direct current to a load R. The rectification circuit REC is composed of, for example, a bridge diode and a capacitor for voltage stabilization (both not shown in the figures). The alternating voltage output from the power receiving coil L2 is subjected to a full-wave rectification by a bridge diode, and then the resultant voltage is stabilized by a capacitor for voltage stabilization. Here, when the apparatus S1 for contactless power transmission is applicable to a power feeding apparatus for supplying power to a moving object such as an electric vehicle, the load R is composed of a charger (not shown) and a battery (not shown) provided in the moving object. The charger functions to control the charging process by charging the battery with a constant current-constant voltage (CCCV) by a direct current rectified by the rectification circuit REC. The battery is not particularly restricted as long as it is capable of saving the power. For example, the battery can be a secondary battery (a lithium ion battery, a lithium polymer battery, a Nickel-Metal Hydride battery or the like) or a capacity element (an electrical double-layered capacitor or the like).

With such a structure, the apparatus S1 for contactless power transmission can be provided, wherein the power is transmitted in a contactless manner from the power feeding coil unit L100 in the power feeding apparatus 100 to the power receiving coil L2 in the power receiving apparatus 200.

(The First Embodiment)

Figure 2:
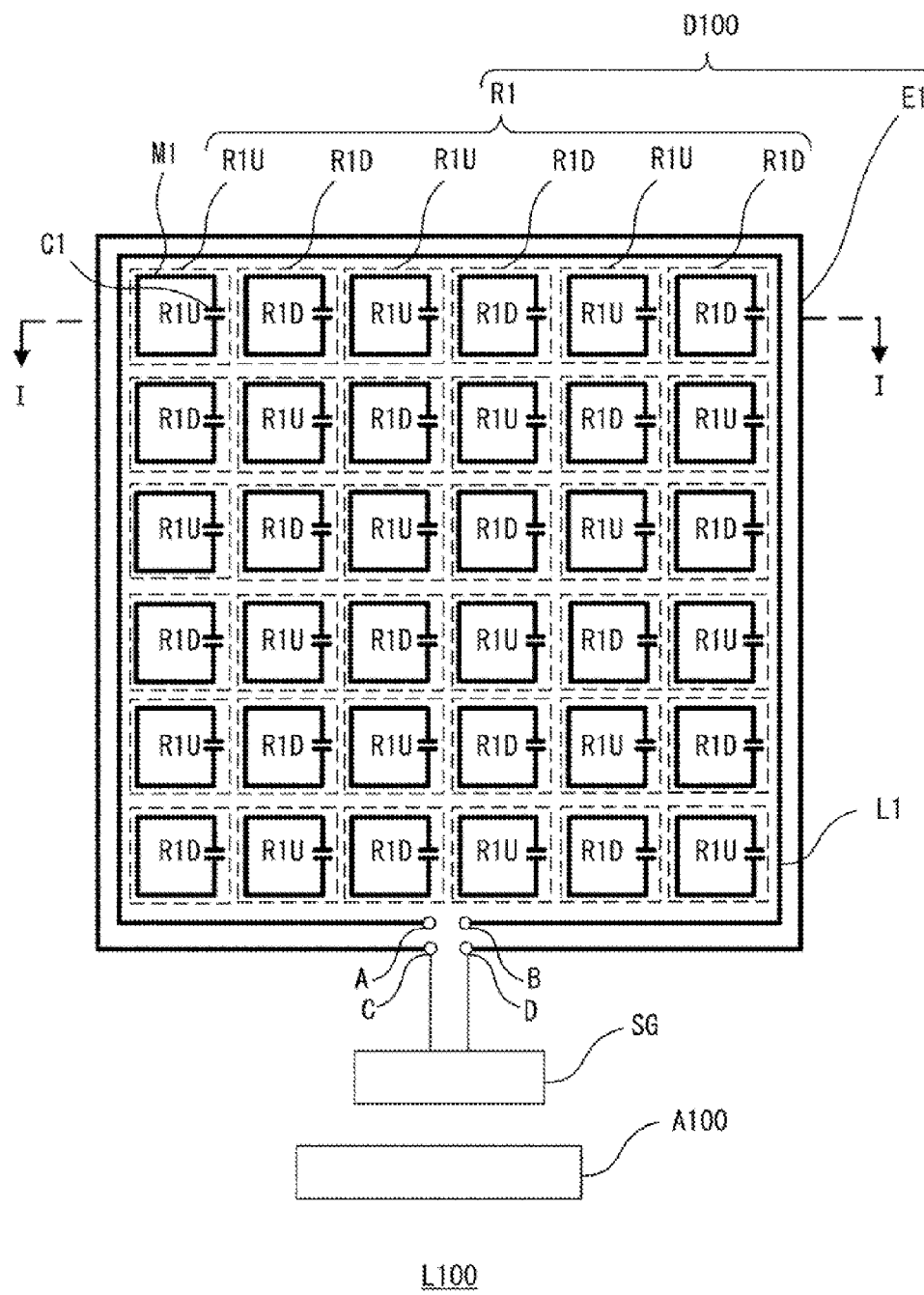
FIG. 2 is a schematic constitutional view showing the power feeding coil unit of the first embodiment viewed from the top in the present invention.
Figure 3:
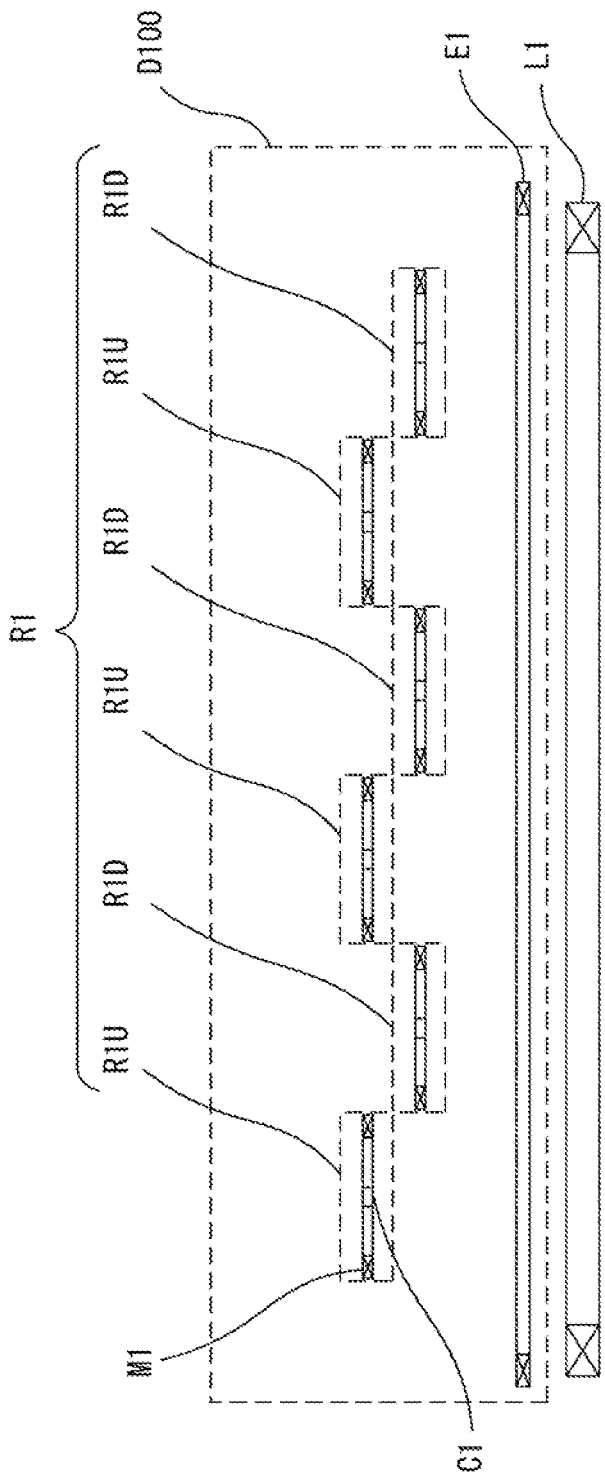
FIG. 3 is a schematic end face view showing the cutting section of the power feeding coil unit along the I-I line in FIG. 2.

Hereinafter, the structure of the power feeding coil unit L100 of the first preferable embodiment of the present invention will be described in detail with reference to FIG. 2 and FIG. 3. FIG. 2 is a schematic constitutional view showing the power feeding coil unit of the first embodiment viewed from the top in the present invention. FIG. 3 is a schematic end face view showing the cutting section of the power feeding coil unit along the I-I line in FIG. 2.

As shown in FIG. 2, the power feeding coil unit L100 is provided with a power feeding coil L1 (the coil for power transmission), an apparatus D100 for detecting foreign matter, a signal generator SG and a frequency response analyzer A100.

As shown in FIG. 2, the power feeding coil L1 is substantially square and is formed by, for example, winding a litz wire into several turns to several dozen of turns, wherein the litz wire is obtained by twisting about 2000 insulated Φ 0.1 (mm) copper lines. In other words, the power feeding coil L1 is one with an in-plane spiral structure. In the power feeding coil L1, the terminal A at the end where the winding starts and the terminal B at the end where the winding ends are connected to the power conversion circuit INV. With such a structure, when the power feeding coil L1 provides an alternating voltage with a given driving frequency from the power conversion circuit INV, an alternating current will flow and an alternating magnetic field will be generated. Then, an electromotive force is generated in the power receiving coil L2 via the alternating magnetic field. That is to say, the power feeding coil L1 functions as one for transmitting power in a contactless manner to the power receiving coil L2. At that time, the driving frequency of the alternating voltage fed to the power feeding coil L1 is set to be, for example, 20 [kHz] to 200 [kHz].

As shown in FIG. 3, the apparatus D100 for detecting foreign matter is disposed at one side of the power feeding coil L1 which faces the power receiving coil L2. That is, the apparatus D100 for detecting foreign matter is disposed between the power feeding coil L1 (power feeding side) and the power receiving coil L2 (power receiving side). For instance, the apparatus D100 for detecting foreign matter is composed of copper-clad multilayered substrates and is provided with a plurality of resonators R1 and an excitation coils E1.

The plurality of resonators R1 are disposed in rows and columns in order to at least cover the area interlinking with the magnetic flux generated by the power feeding coil L1. In other words, the plurality of resonators R1 are placed in rows and columns in the in-plane direction as shown in FIG. 2. More specifically, the plurality of resonators R1 are disposed to cover the area defined by the wound wires of the power feeding coil L1. In the present embodiment, 36 resonators R1 are placed in 6 rows×6 columns. That is, the area where the plurality of resonators R1 are disposed becomes the area for metal detection. The plurality of resonators R1 are each formed by each resonance coil M1 and each resonance capacitor C1. As shown in FIG. 2, the resonance coil M1 presents to be substantially square and is formed by, for example, pattern printing 4 turns of coils on a layer of the copper-clad multilayered substrate at the side of the power receiving coil L2 in a direction in which the power feeding coil L1 faces the power receiving coil L2. The resonance capacitor C1 and the resonance coil M1 are connected in series to form a resonance circuit. The resonance capacitor C1 can be, for example, a stacked ceramic capacitor, and the electrostatic capacity of the resonance capacitor C1 is set to be several hundreds of picofarad to several thousands of picofarads. Further, if a minute foreign metal is to be detected such as a coin of about Φ 10 mm, each resonator R1 can be made as a substantial square with a size of 10 mm×10 mm. In addition, the plurality of resonators R1 can also be disposed in rows and columns to cover a wider area than that defined by the wound wire of the power feeding coil L1. In that case, not only the foreign matter on the power feeding coil L but also those surrounding the power feeding coil L1 can be detected. Anyway, if the area where the plurality of resonators R1 are disposed in rows and columns can cover at least the area interlinking with the magnetic flux generated by the power feeding coil L1, it can be set at will.

The plurality of resonators R1 with the structure mentioned above are disposed in layers. In the present embodiment, the plurality of resonators R1 are disposed in two layers. Specifically, the plurality of resonators R1U are disposed at the side of the power receiving coil L2 in a direction in which the power feeding coil L1 faces the power receiving coil L2 while the plurality of resonators R1D are disposed at the side of the power feeding coil L1 in a direction in which the power feeding coil L faces the power receiving coil L2. As shown in FIG. 2, the plurality of resonators R1U and R1D are alternatively disposed in the column direction and the row direction and do not overlap when viewed in a direction from the power feeding coil L1 towards the power receiving coil L2. In other words, the resonators R1D are disposed to be adjacent to the resonators R1U in the row direction and the column direction. That is, the distance between each of the plurality of resonators R1U and R1D and the excitation coil E1 to be described later is different from each other, wherein the plurality of resonators R1U and the plurality of resonators R1D are disposed to be adjacent in the row direction and the column direction. With the configuration described above, the influence of mutual inductance becomes weaker in the plurality of resonators R1U and the plurality of resonators R1D. In addition, it is preferable that in the whole area for metal detection the plurality of resonators R1 disposed to be adjacent in the row direction and the column direction do not overlap when viewed in a direction perpendicular to the surface and the distances to the excitation coil E1 which is to be described later is different from each other. However, if the effect of the present invention can be obtained, the plurality of resonators R1 can be disposed as follows. Specifically, in part of the area for metal detection, the plurality of resonators R1 disposed to be adjacent in the row direction and the column direction can overlap when viewed in a direction perpendicular to the surface and the distance between each resonator and the excitation coil E1 can be almost the same.

Furthermore, in the plurality of resonators R1U and R1D, the inductance of the resonance coil M1 is the same in each resonator, and the electrostatic capacity of the resonance capacitor C1 is also the same in each resonator. Thus, the resonance frequencies Fr of the plurality of resonators come to the same one. In the present embodiment, the resonance frequency Fr of the plurality of resonators R1U and R1D is set to be, for example, 6000 [kHz]. In other words, the plurality of resonators R1U and the plurality of resonators R1D, disposed to be adjacent in the row direction and the column direction when viewed in a direction in which the power feeding coil L1 faces the power receiving coil L2, all have a same resonance frequency fr. Here, if the resonators with the same resonance frequency are disposed to be adjacent in the row direction and the column direction in the same layer, the resonance coils of the adjacent resonance resonators will be magnetically coupled, then the mutual inductance will change and several resonance frequencies will generate. In addition, a problem rises that the Q value of the resonance coil in each resonator will significantly decrease. In contrast, in the present embodiment, the plurality of resonators R1U and the plurality of resonators R1D which are adjacent in the row direction and the column direction are disposed to have a weaker influence of mutual inductance. In this respect, the plurality of resonators R1U and the plurality of resonators R1D which are adjacent in the row direction and the column direction will not affect each other and the change of the mutual inductance will be inhibited. In addition, the Q value of the resonance coil M1 in the resonator R1U and that of the resonance coil M1 in the resonator R1D are prevented from decreasing. Further, it is preferable that in the whole area for metal detection the plurality of resonators R1U and the plurality of resonators R1D disposed to be adjacent in the row direction and the column direction are disposed to decrease the influence of the mutual inductance. However, if the effect of the present invention can be obtained, the plurality of resonators R1U and the plurality of resonators R1D can also be disposed to have mutual influence of the mutual inductance in part of the area for metal detection.

As shown in FIG. 2, the excitation coil E1 is substantially square and is formed by, for example, pattern printing 3 turns of coils on a layer of the copper-clad multilayered substrate at the side of the power receiving coil L1 in a direction in which the power feeding coil L1 faces the power receiving coil L2. The pattern of the excitation coil E1 is formed outside the area defined by the wound wire of the power feeding coil L1. Also, the end where the pattern of the excitation coil E1 starts (i.e., the terminal C) and the end where the pattern ends (i.e., the terminal D) are connected to the signal generator SG which is to be described later. With such a structure, the excitation coil E1 is capable of receiving the sine wave signals output by the signal generator SG and is then excited to generate a magnetic field. As such, the resonance coils M1 of the plurality of resonators R1U and R1D will be excited by the magnetic field generated by the excitation coil E1.

The signal generator SG continuously provides the sine wave signals of a single frequency to the excitation coil E1. The single frequency of the sine wave signals is set to be the same as that of the resonance frequency fr of the plurality of resonators R1U and R1D. In the present invention, the excitation coil E1 receives the sine wave signals from the signal generator SG and is then excited to generate a magnetic field. An electromotive force is generated in the resonance coils M1 of the plurality of resonators R1U and R1D via this magnetic field, and then the current flows. At this time, as the resonance frequency is set to be 6000 [kHz], the plurality of resonators R1U and R1D come into a resonance state when the signal generator SG outputs the sine wave signals of 6000 [kHz], and a resonance current flows as well. As such, the single frequency of the sine wave signals with which the signal generator SG is set as a high one having an order of magnitude different from that of the driving frequency of the power feeding coil L1. In other words, the single frequency of the sine wave signals output from the signal generator SG with which the excitation coil E1 is excited is set to be within a frequency band in which the power feeding coil L1 will not be excited.

When the driving frequency of the power feeding coil L is close to the single frequency of the sine wave signals output from the signal generator SG with which the excitation coil E1 is excited, the excitation coil M1 of the plurality of resonators R1U and R1D is excited by the intense magnetic field generated by the power feeding coil L1 for power transmission. Thus, a high current will flow to the plurality of resonators R1U and R1D and damages may happen. In addition, in the present embodiment, the single frequency of the sine wave signals output from the signal generator SG with which the excitation coil E1 is excited is set as a high one having an order of magnitude different from that of the driving frequency of the power feeding coil L1, i.e., a frequency band in which the power feeding coil L1 will not be excited, and the plurality of resonators R1U and R1D have a high impedance with respect to the intense magnetic field generated by the power feeding coil L11 for power transmission so that no current will flow. Further, the plurality of resonators R1U and R1D are only tuned with the single frequency of the sine wave signals output from the signal generator SG with which the excitation coil E1 is excited so that the plurality of resonators R1U and R1D are excited and a current flows. Therefore, the damage due to the large current flowing to the plurality of resonators R1U and R1D can be prevented. In addition, in the present embodiment, the single frequency of the sine wave signals output from the signal generator SG with which the excitation coil E1 is excited is set as one having an order of magnitude higher than that of the driving frequency of the power feeding coil L1. However, this frequency is not limited thereto and can be also set as one having an order of magnitude lower than that of the driving frequency of the power feeding coil L1. Anyway, the single frequency of the sine wave signals output from the signal generator SG with which the excitation coil E1 is excited can be set to be within a frequency band in which the power feeding coil L1 will not be excited.

The frequency response analyzer A100 is connected to two terminals in the resonance capacitor C1 of the plurality of resonators R1U and R1D. If the frequency response analyzer A100 is used, the impedance value and the Q value of the plurality of resonators R1U and R1D can be measured. In the present embodiment, the frequency response analyzer A100 is used to detect the foreign metals. Specifically, the impedance value and the Q value at the resonance frequency of the resonator R1U and R1D when no foreign metal is present are memorized. Then, the impedance values and Q values measured by the frequency response analyzer A100 are used in the comparison and the presence of the foreign metals can be determined based on the changes of these values. More specifically, if a foreign metal is present, the impedance value as measured by the frequency response analyzer A100 will increase and the Q value will decrease. If thresholds capable of determining whether a foreign metal are present or not is predetermined in advance with respect to the impedance value and the Q value, then the presence of a foreign metal can be determined based on these thresholds. In this respect, if the frequency response analyzer A100 is used to measure the electric properties of the plurality of resonators R1U and R1D (i.e., the impedance value and the Q value), it is easy to detect the foreign metals.

As described above, in the power feeding coil unit L100 of the present embodiment, the plurality of resonators R1U and R1D are disposed to cover at least the area interlinking with the magnetic flux generated by the power feeding coil L and to decrease the influence of the mutual inductance. Thus, even if the plurality of resonators R1U and R1D are disposed without gaps in the area for metal detection, each resonator R1U, R1D can be prevented from influencing each other. In this respect, each resonator R1U, R1D is prevented from generating multiple resonance frequencies and the decrease of Q value will be inhibited. As a result, the accuracy in detecting metals will be improved when the power is transmitted in a contactless manner.

Further, in the power feeding coil unit L100 of the present embodiment, the plurality of resonators R1U and R1D are disposed in rows and columns to cover at least the area interlinking with the magnetic flux generated by the power feeding coil L1, and the plurality of resonators R1U and R1D disposed to be adjacent in the row direction and the column direction are disposed in layers, wherein the plurality of resonators do not overlap when viewed in a direction perpendicular to the surface and the distance between each resonator and the excitation coil is different from each other. Thus, even if the plurality of resonators R1U and R1D are disposed without gaps in the area for metal detection, each resonator R1U, R1D can be prevented from influencing each other. In this respect, each resonator R1U, R1D is prevented from generating multiple resonance frequencies and the decrease of Q value will be inhibited. As a result, the accuracy in detecting foreign matter will be improved when the power is transmitted in a contactless manner.

(The Second Embodiment)

Figure 4:
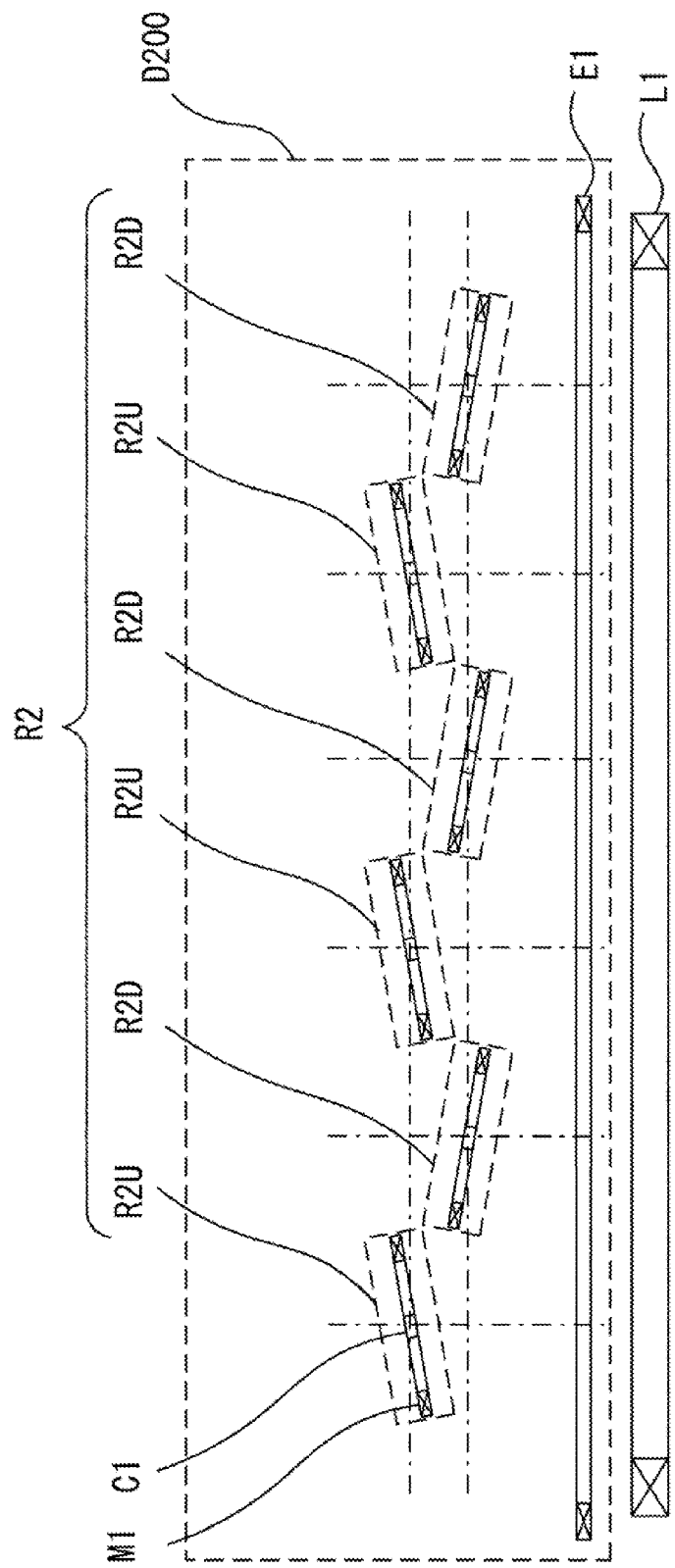
FIG. 4 is a schematic end face view showing the cutting section of the power feeding coil unit in the second embodiment of the present invention, which corresponds to the schematic end face view in FIG. 3 showing the cutting section of the power feeding coil unit in the first embodiment of the present invention along the I-I line in FIG. 2.

Hereinafter, the structure of the power feeding coil unit L200 in the second embodiment of the present invention will be described in detail with reference to FIG. 4. FIG. 4 is a schematic end face view showing the section of the power feeding coil unit in the second embodiment of the present invention, corresponding to the schematic end view in FIG. 3 showing the cutting section of the power feeding coil unit in the first embodiment of the present invention along the I-I line in FIG. 2.

As the same as the power feeding coil unit L100 in the first embodiment, the power feeding coil unit L200 is provided with a power feeding coil L1, an apparatus D200 for detecting foreign matter, a signal generator SG and a frequency response analyzer A100. The structures of the power feeding coil L1, the signal generator SG and the frequency response analyzer A100 are the same with those in the power feeding coil unit L100 of the first embodiment. In the present embodiment, what is different from the first embodiment is the structure of the resonance coil M1 of the plurality of resonators R1 in the apparatus D200 for detecting foreign matter. Hereinafter, the description will be focused on the points different from those of the first embodiments.

As shown in FIG. 4, the apparatus D200 for detecting foreign matter is disposed on one side of the power feeding coil L1 at the side facing the power receiving coil L2. That is, the apparatus D200 for detecting foreign matter is disposed between the power feeding coil L1 (power feeding side) and the power receiving coil L2 (power receiving side). The apparatus D200 for detecting foreign matter is formed by, for example, a copper-clad multilayered substrate and is provided with a plurality of resonators R2 and an excitation coil E1.

The plurality of resonators R2 are disposed in rows and columns to cover at least the area interlinking with the magnetic flux generated by the power feeding coil L1. In other words, the plurality of resonators R2 is disposed in rows and columns in the in-plane direction. In addition, the plurality of resonators R2 are disposed in layers. In the present embodiment, the plurality of resonators R2 are disposed in two layers. Specifically, the plurality of resonators R2U are disposed at the side of the power receiving coil L2 in a direction in which the power feeding coil L1 faces the power receiving coil L2 while the plurality of resonators R2D are disposed at the side of the power feeding coil L1 in a direction in which the power feeding coil L1 faces the power receiving coil L2. The plurality of resonators R2U and R2D are the same as those in the power feeding coil unit L100 of the first embodiment. The distance between each of the plurality of resonators R2U and R2D and the excitation coil E1 is different from each other, wherein the plurality of resonators R1U and the plurality of resonators R1D are disposed to be adjacent in the row direction and the column direction. Each of the plurality of resonators R2U and R2D is composed of a resonance coil M1 and a resonance capacitor C1. In the present embodiment, the axis of the resonance coil M1 in each of the plurality of resonators R2U and R2D inclines with respect to the axis of the excitation coil E1. This will be described in detail with reference to FIG. 4. Further, as in the first embodiment, the plurality of resonators R2 can be disposed in rows and columns to cover a wider area than that defined by the wound wire of the power feeding coil L1. In this case, not only the foreign matter on the power feeding coil L1 but also those surrounding the power feeding coil L1 can be detected. Anyway, if the area where the plurality of resonators R2 are disposed in rows and columns can cover at least the area interlinking with the magnetic flux generated by the power feeding coil L1, it can be set at will. In addition, it is preferable that in the whole area for metal detection the plurality of resonators R2 disposed to be adjacent in the row direction and the column direction do not overlap when viewed in a direction perpendicular to the surface and the distances to the excitation coil E1 are different from each other. However, if the effect of the present invention can be obtained, the plurality of resonators R2 can be disposed as follows. Specifically, in part of the area for metal detection, the plurality of resonators R2 disposed to be adjacent in the row direction and the column direction can overlap when viewed in a direction perpendicular to the surface and the distances to the excitation coil E1 can be almost the same.

As shown in FIG. 4, in the plurality of resonators R2U, the axis of the resonance coil M1 in each resonator inclines to the left side of the figure with respect to the axis of the excitation coil E1. In addition, as shown in FIG. 4, in the plurality of resonators R2D, the axis of the resonance coil M1 in each resonator inclines to the right side of the figure with respect to the axis of the excitation coil E1. That is, in the plurality of resonators R2U and the plurality of resonators R2D disposed to be adjacent in the column direction and the row direction, the axis of the resonance coil M1 in each resonator R2U inclines with respect to the axis of the excitation coil E1 in a direction opposite to that in each resonator R2D. Thus, in the plurality of resonators R2U and the plurality of resonators R2D disposed to be adjacent in the column direction and the row direction, the magnetic coupling between the plurality of resonators R2U and the plurality of resonators R2D becomes weaker and the change of the mutual inductance is inhibited. Also, multiple resonance frequencies can be effectively prevented from generating. In addition, the decrease of both the Q value of the resonance coil M1 in the resonators R2U and that in the resonators R2D can be inhibited at the same time.

With respect to the power feeding coil unit L200 of the present embodiment as described above, in the plurality of resonators R2U and R2D disposed to be adjacent in the column direction or the row direction, the axis of the resonance coil M1 in each resonator R2U inclines with respect to the axis of the excitation coil E1 in a direction opposite to that in each resonator R2D. Thus, even if the plurality of resonators R2U and R2D are disposed without gaps in the area for metal detection, each resonator R2U, R2D can be prevented from influencing each other. In this respect, each resonator R2U, R2D can be effectively prevented from generating multiple resonance frequencies and the decrease of the Q value will be further inhibited. Therefore, the accuracy in detecting metals can be further improved when the power is transmitted in a contactless manner.

(The Third Embodiment)

Hereinafter, the structure of the power feeding coil unit L300 in the third embodiment of the present invention will be described in detail with reference to FIG. 5 to FIG. 7.

Figure 5:
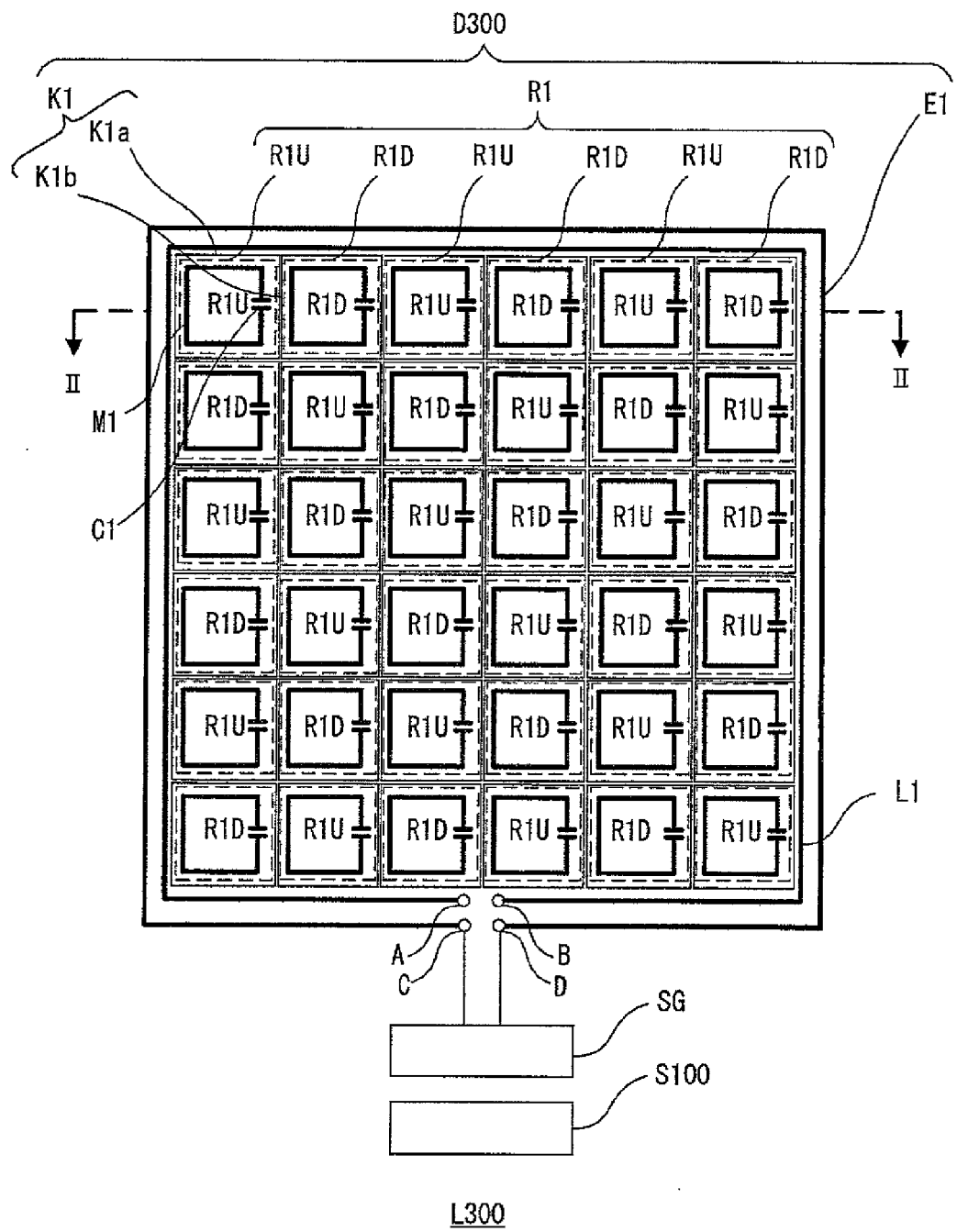
FIG. 5 is a schematic constitutional view showing the power feeding coil unit of the third embodiment viewed from the top in the present invention.

FIG. 5 is a schematic constitutional view showing the power feeding coil unit of the third embodiment viewed from the top in the present invention. FIG. 6 is a schematic end face view showing the cutting section of the power feeding coil unit along the II-II line in FIG. 5. FIG. 7 is a schematic constitutional view showing the signal generator, the apparatus for detecting foreign matter and the system for detecting foreign matter in the power feeding coil unit of the third embodiment of the present invention.

As the same as the power feeding coil unit L100 of the first embodiment, the power feeding coil unit L300 is provided with a power feeding coil L1, an apparatus D300 for detecting foreign matter, a signal generator SG and a system S100 for detecting foreign matter. The structures of the power feeding coil L1 and the signal generator SG are the same with those in the power feeding coil unit L100 of the first embodiment. In the present embodiment, what is different from the first embodiment is that the apparatus D300 for detecting foreign matter is provided with a plurality of detecting coils K1 and the system S100 for detecting foreign matter is disposed instead of the frequency response analyzer A100. Hereinafter, the description will be focused on the points different from those of the first embodiments.

Figure 6:
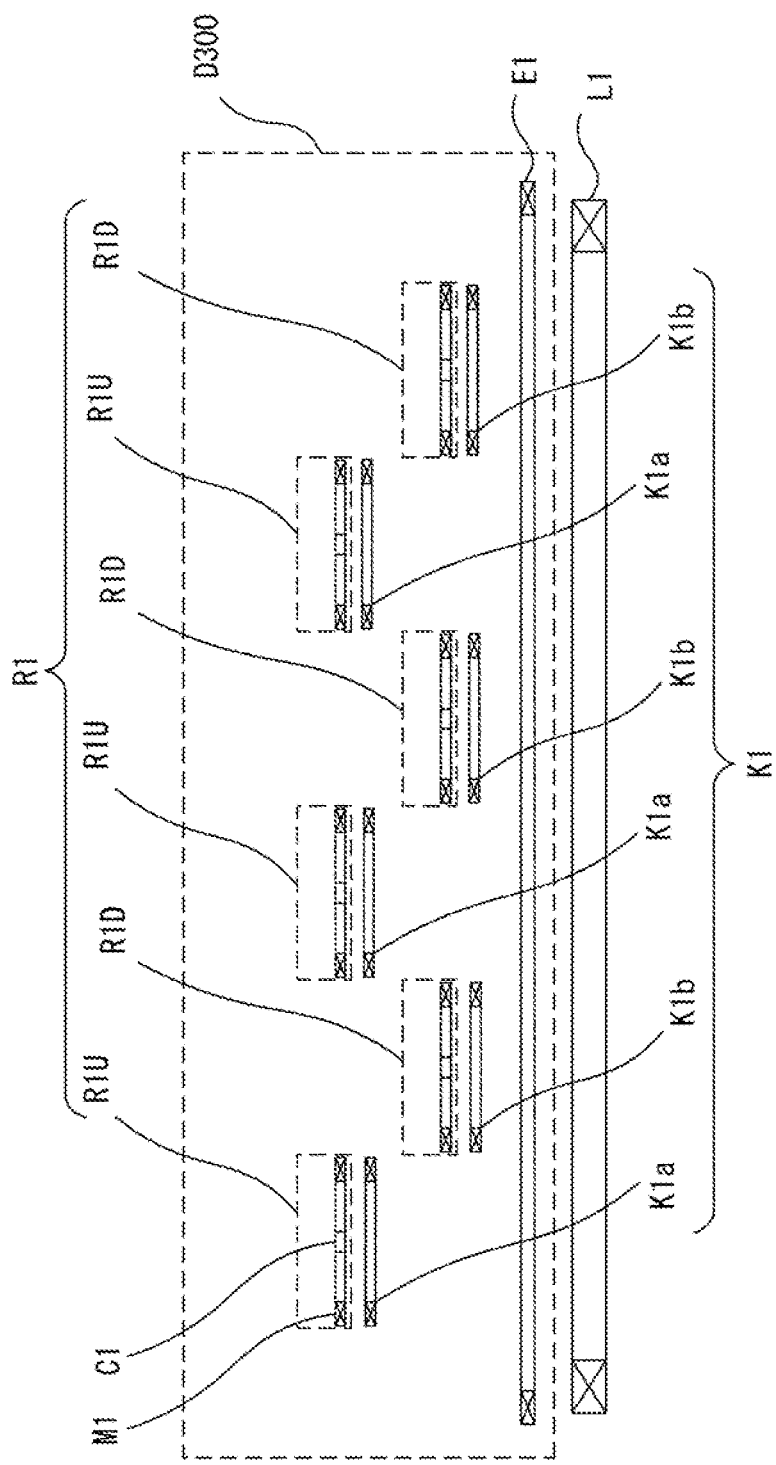
FIG. 6 is a schematic end face view showing the cutting section of the power feeding coil unit along the II-II line in FIG. 5.

As shown in FIG. 6, the apparatus D300 for detecting foreign matter is disposed on the power feeding coil L1 at the side facing the power receiving coil L2. That is, the apparatus D300 for detecting foreign matter is placed between the power feeding coil L1 and the power receiving coil L2. The apparatus D300 for detecting foreign matter is formed by, for example, a copper-clad multilayered substrate and is provided with a plurality of resonators R1, an excitation coil E1 and a plurality of detecting coils K1. The structures of the plurality of resonators R1 and the excitation coil E1 are the same with those in the power feeding coil unit L100 of the first embodiment.

As shown in FIG. 5, each of the plurality of detecting coils K1 presents to be substantially square and is formed by, for example, pattern printing 4 turns of coils on a layer of the copper-clad multilayered substrate between the layer where the excitation coil M1 of the plurality of resonators R1 is formed and the layer where the excitation coil E1 is formed in a direction in which the power feeding coil L1 faces the power receiving coil L2. Each pattern of the plurality of detecting coils K1 is disposed in rows and columns to be electromagnetically (magnetically) coupled to each of the plurality of resonators R1. That is, each pattern of the plurality of detecting coils K1 faces each resonance coil M1 of the plurality of resonators R1. In addition, if the axis of each pattern in the plurality of detecting coils K1 is consistent with that of each resonance coil M1 in the plurality of resonators R1, then the electromagnetic coupling will be strong, which is preferable. The plurality of detecting coils K1 are electromagnetically coupled to each of the plurality of resonators R1, so the alternating current flows to the resonator excited by the excitation coil E1 so that the electromotive force is generated and the alternating current flows. As such, the alternating signal Vk is output to a plurality of AC/DC converter CONV to be described later from the plurality of detecting coils K. At that time, the detecting coil K1a disposed opposing to the resonator R1U outputs an alternating current signal Vk1 and the detecting coil K1b disposed opposing to the resonator R1D outputs an alternating current signal Vk2.

Figure 7:
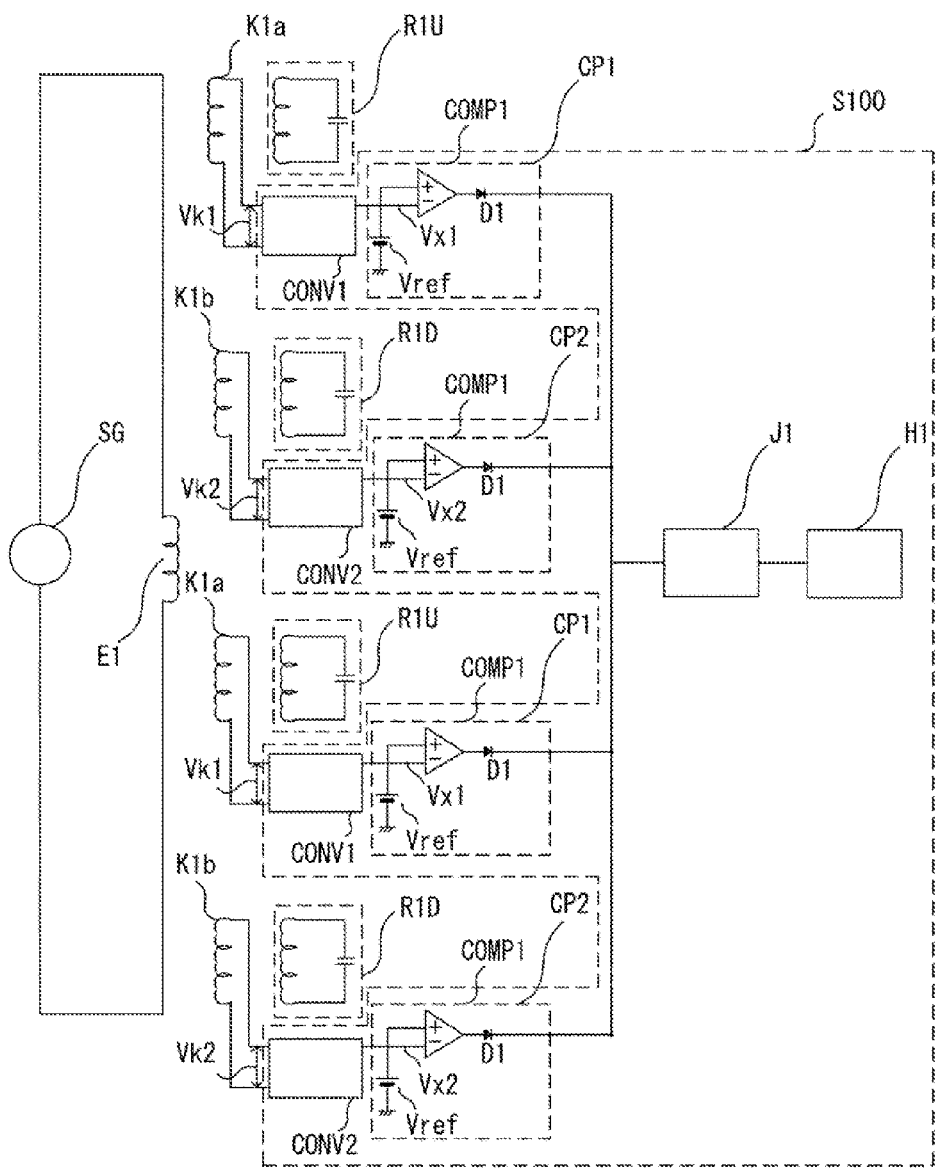
FIG. 7 is a schematic constitutional view showing the signal generator, the apparatus for detecting foreign matter and the system for detecting foreign matter in the power feeding coil unit of the third embodiment of the present invention.

As shown in FIG. 7, the system S100 for detecting foreign matter is provided with a plurality of AC/DC converters CONV, a plurality of comparator circuits CP, a decider J1 and a display H1. In the present embodiment, the system for detecting foreign matter with two resonators R1U and two resonators R1D are shown in the figures. However, the system S100 for detecting foreign matter can also be composed of a plurality of resonators R1U and R1D.

The plurality of AC/DC converters CONV are connected to both ends of each coil among the plurality of detecting coils K1. The plurality of AC/DC converters CONV converts the alternating current signal Vk output from the plurality of detecting coils K1 into a direct current signal Vx and then outputs the direct current signal Vx to the plurality of comparator circuits CP which are to be described later. Specifically, the plurality of AC/DC converters CONV are provided with a plurality of AC/DC converters CONV1 connected to the detecting coil K1a and a plurality of AC/DC converters CONV2 connected to the detecting coil K1b. Further, the alternating current signal Vk1 is converted to a direct current signal Vx1 by the plurality of AC/DC converters CONV1, and the alternating current signal Vk2 is converted to a direct current signal Vx2 by the plurality of AC/DC converters CONV2.

As shown in FIG. 7, the plurality of comparator circuits CP are respectively composed of a comparator COMP1 and a diode D1. The direct current signal Vx output from the plurality of AC/DC converters CONV is input to the inverted input terminal of the comparator COMP1, and the reference voltage Vref is input into the non-inverted input terminal of the comparator COMP1. The positive terminal of the diode D1 is connected to the output terminal of the comparator COMP1. In addition, each negative terminal of the diode D1 is connected to the decider J1 which is to be described later. The plurality of comparator circuits CP with such a structure compares the direct current signal Vx input to the inverted input terminal of the comparator COMP1 with the reference voltage Vref input to the non-inverted input terminal. When the direct current signal Vx is higher than the reference voltage Vret; a signal of a low level is output from the output terminal of the comparator COMP1 to the decider J1 to be described later via the diode D1. In contrast, when the direct current signal Vx is lower than the reference voltage Vref, a signal of a high level is output from the output terminal of the comparator COMP1 to the decider J1 to be described later via the diode D1. Specifically, the plurality of comparator circuits CP are provided with a plurality of comparator circuits CP1 where the direct current signal Vx1 output from the plurality of AC/DC converters CONV1 is input to the inverted input terminal of the comparator COMP1 and a plurality of comparator circuits CP2 where the direct current signal Vx2 output from the plurality of AC/DC converters CONV2 is input to the inverted input terminal of the comparator COMP1.

The decider J1 is connected to the plurality of comparator circuits CP. In this way, since the decider J1 is jointly connected to the plurality of comparator circuits CP, when all the signals output from the plurality of comparator circuits CP have a low level, a signal of a low level is input to the decider J1. In addition, when any of the signals output from the plurality of comparator circuits CP has a high level, a signal of a high level is input to the decider J1. Specifically, when the signal generator SG outputs a sine wave signal of 6000 [kHz], if all the signals as the result of the comparison between the direct current signal Vx of the plurality of comparator circuits CP1 and the reference voltage Vref have a low level, the decider J1 determines that no foreign metal is present. Otherwise, when any one of the signals as the result of the comparison between the direct current signal Vx of the plurality of comparator circuits CP1 and the reference voltage Vref has a high level, it is decided that a foreign metal is present. In this way, the decider J1 analyzes the wave form of the signal output from the plurality of comparator circuits CP to determine whether a foreign metal is present. Then, the result (whether a foreign metal is present or not) from the decider J1 is output to the display H1.

The display H1 is connected to the decider J1. The display H1 is capable of telling the users the result (whether a foreign metal is present or not) given by the decider J1. For example, the display H1 is provided with indicator lights with colors like red and green (not shown) and can be performed as described below. That is, if the decider J1 determines that no foreign metal has been detected, then the green indicator light is lighted. If the decider J1 determines that a foreign metal has been detected, then the red indicator light is lighted. As such, the user is informed of the presence of a foreign metal by the display H1 so that the user is enabled to intervene in the power supply of the apparatus S1 for contactless power transmission (keep it on or stop it). Further, other means in which the presence of the foreign metal is not determined by the decider J1 and the display H1 can be performed as described below. That is, when the plurality of comparator circuits CP output a signal of a low level, the action of the power conversion circuit INV is kept on. When the plurality of comparator circuits CP output a signal of a high level, the action of the power conversion circuit INV is stopped.

Figure 8:
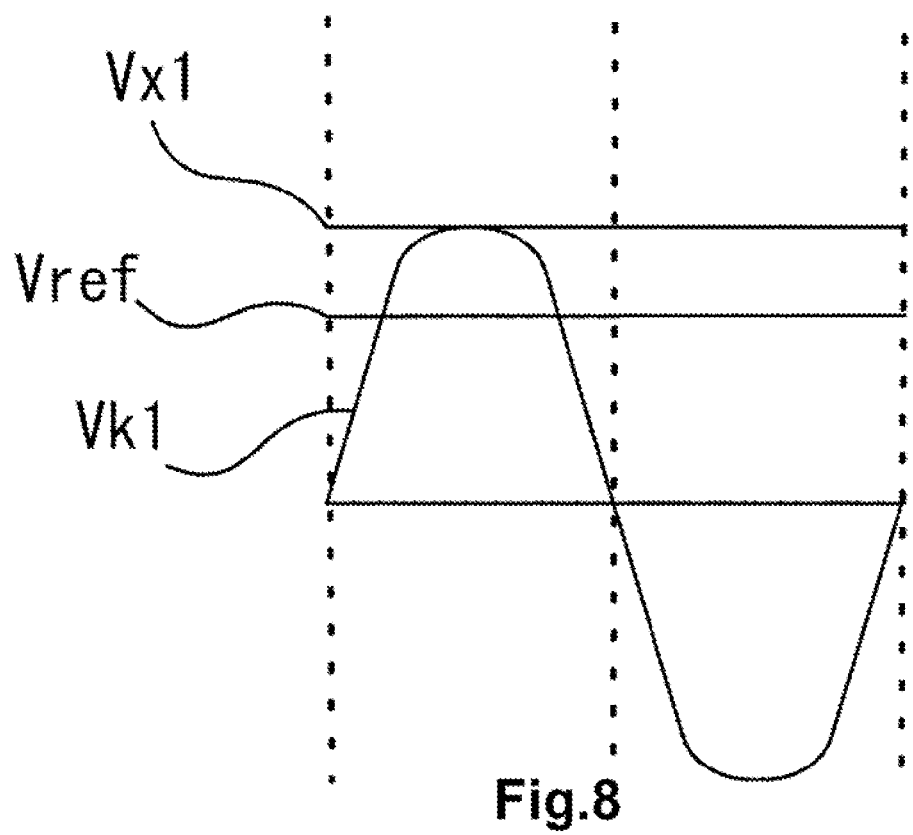
FIG. 8 is a waveform diagram illustrating the waveform of the signals output from a plurality of detecting coils and a plurality of AC/DC converter when the signal generator outputs sine wave signals of 6000 [kHz].
Figure 9:
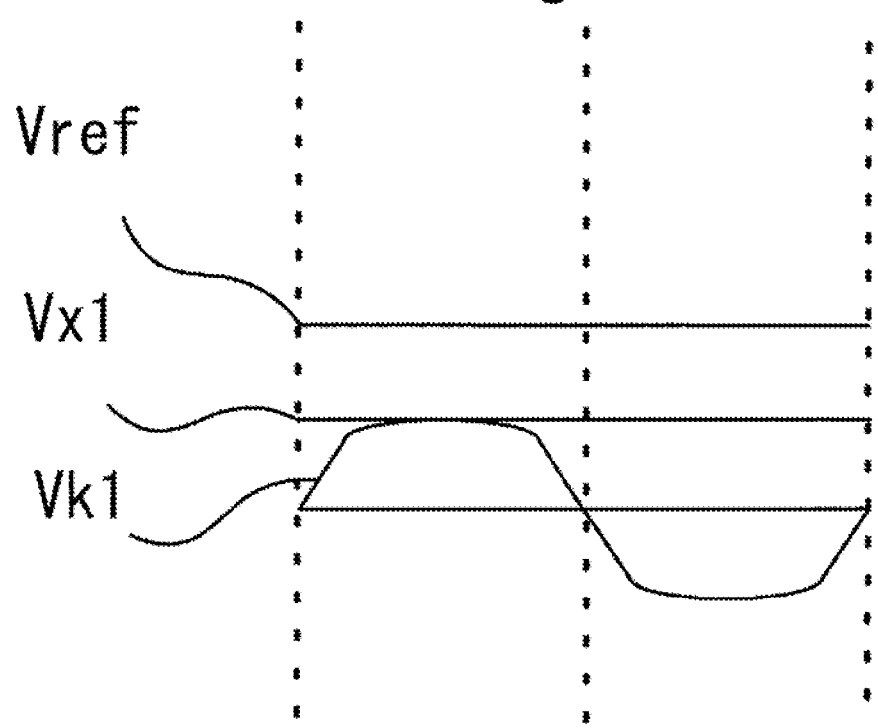
FIG. 9 is a waveform diagram illustrating the waveform of the signals output from a plurality of detecting coils and a plurality of AC/DC converter when the signal generator outputs sine wave signals of 6000 [kHz].

Here, the waveform of the signal from the system S100 for detecting foreign matter in the power feeding coil unit L300 of the present embodiment will be described below with reference to FIG. 8 and FIG. 9. FIG. 8 and FIG. 9 are waveform diagrams illustrating the waveform of the signals output from the plurality of detecting coils and the plurality of AC/DC converter when the signal generator outputs sine wave signals of 6000 [kHz]. Here, the waveform of the signals output from the detecting coils K1a and the plurality of AC/DC converters CONV1 when the signal generator outputs sine wave signals of 6000 [kHz] will be described as follows. The description about the waveform of the signals output from the detecting coil K1b and the plurality of AC/DC converters CONV2 will be omitted as the waveform is the same as that of the signals output from the detecting coil K1a and the plurality of AC/DC converters CONV1.

If the sine wave signal of 6000 [kHz] is supplied to the excitation coil E1 from the signal generator SG, the plurality of resonators R1U come into the resonance state and an resonance current flows. Also, electromotive forces are generated in the plurality of detecting coils K1a respectively disposed with respect to the plurality of resonators R1U, and an alternating current flows. The alternating current signal Vk is output to the plurality of AC/DC converter CONV1 from the plurality of detecting coil K1a and then converted to the direct current signal Vx1 by the plurality of AC/DC converter CONV1. In this way, the plurality of comparator circuits CP1 compare the direct current signal Vx input to the inverted input terminal of the comparator COMP1 and the reference voltage Vref input to the non-inverted input terminal. Here, as shown in FIG. 8, when no foreign metal is present, the direct current signal Vx1 becomes higher than the reference voltage Vref so that a signal of a low level is output from the comparator circuit CP1. Further, when a foreign metal is present, the resonance frequencies of the plurality of resonator R1U become higher than 6000 [kHz]. At the same time, the Q value decreases and the direct current signal Vx1 becomes lower than the reference voltage Vref as shown in FIG. 9. Thus, a signal of a high level is output from the comparator circuit CP2.

As described above, the power feeding coil L300 of the present embodiment can be disposed as follows. Specifically, the apparatus D300 for detecting foreign matter is further provided with a plurality of detecting coils K1 and the plurality of detecting coils K1 are respectively electromagnetically coupled to each of the plurality of resonators R1. In this case, as the means for measuring the Q value is not directly connected to the plurality of resonators R1 and it is possible to measure the Q values of the plurality of resonators R1, the decrease of the Q values of the plurality of resonators R1 can be further inhibited without changing the resonance frequencies of the plurality of resonators R1.

Furthermore, the present invention does not have to be not limited to the described embodiments, and various modifications within the spirit of the invention are practical. For example, the present embodiment is described by using an example in which an apparatus for detecting foreign matter is applied to a coil unit for contactless power transmission from power feeding side to power receiving side. However, the present invention is not limited thereto. The apparatus for detecting foreign matter of the present invention can also be used to detect the foreign metals present in the food, medicines and industrial materials which are wrapped in packing materials.

The coil unit of the present invention can be used in an apparatus for detecting foreign matter, equipped on contactless power feeding device for electric vehicle, which is used for power transmission and charging of the secondary battery in a contactless manner from the ground to a parking electric vehicle. The coil unit of the present invention can also be used in an apparatus for detecting foreign matter used to detect the foreign metals present in the food, medicines and industrial materials which are wrapped in packing materials.

DESCRIPTION OF REFERENCE NUMERALS

100 power feeding apparatus
200 power receiving apparatus
A to D terminal
A100 frequency response analyzer
C1 resonance capacitor
COMP1 comparator
CONV, CONV1, CONV2 plurality of AC/DC converters
CP, CP1, CP2 plurality of comparator circuits
D1 diode
D100, D200, D300 the apparatus for detecting foreign matter
E1 excitation coil
H1 display
INV power conversion circuit
J1 decider
K1, K1a, K1b plurality of detecting coils
L1 power feeding coil
L100, L200, L300 power feeding coil unit
L2 power receiving coil
M1 resonance coil
R1, R1U, R1D, R2, R2U, R2D plurality of resonators
REC rectification circuit
S1 the apparatus for contactless power transmission
S100 the system for detecting foreign matter
SG, SG2 signal generator
VG voltage source

What is claimed is:

1. A coil unit, which is used for a contactless power transmission from a power feeding side to a power receiving side, comprising a coil for power transmission and an apparatus for detecting foreign matter,
    wherein, the apparatus for detecting foreign matter comprises a plurality of resonators comprising a resonance coil and a resonance capacitor, and an excitation coil that generates a magnetic field for exciting the plurality of resonators,
    wherein, the plurality of resonators are disposed so as to cover at least an area interlinking with a magnetic flux generated by the coil for power transmission and to decrease an influence of mutual inductance between the plurality of resonators, and
    wherein, the plurality of resonators adjacent with each other in a column direction or a row direction are disposed in different layers in a layering direction perpendicular to the column direction and the row direction, and the plurality of resonators do not overlap with each other when viewed from the layering direction.

2. A coil unit, which is used for a contactless power transmission from a power feeding side to a power receiving side, comprising a coil for power transmission and an apparatus for detecting foreign matter,
    wherein, the apparatus for detecting foreign matter comprises a plurality of resonators comprising a resonance coil and a resonance capacitor, and an excitation coil that generates a magnetic field for exciting the plurality of resonators,
    wherein, the plurality of resonators are disposed in rows and columns so as to cover at least an area interlinking with a magnetic flux generated by the coil for power transmission,
    wherein, the plurality of resonators adjacent with each other in a column direction or a row direction are disposed in different layers in a layering direction perpendicular to the column direction and the row direction, the plurality of resonators do not overlap with each other when viewed from the layering direction and the distances from the resonators to the excitation coil are different from each other.

3. The coil unit of claim 2, wherein,
    in the plurality of resonators disposed adjacent with each other in the column direction or the row direction, an axis of the resonance coil in each resonator inclines in a direction opposite to each other with respect to an axis of the excitation coil.

4. The coil unit of claim 1, wherein,
    the apparatus for detecting foreign matter further comprises a plurality of detecting coils,
    each of the plurality of detecting coils is disposed so as to be magnetically coupled to each resonator of the plurality of resonators.

5. An apparatus for detecting foreign matter, comprising a plurality of resonators comprising a resonance coil and a resonance capacitor, and an excitation coil that generates a magnetic field for exciting the plurality of resonators,
    the plurality of resonators being disposed in rows and columns in an in-plane direction,
    wherein, the plurality of resonators adjacent with each other in a column direction or a row direction are disposed in different layers in a layering direction perpendicular to the column direction and the row direction, the plurality of resonators do not overlap with each other when viewed from the layering direction and the distances from the resonators to the excitation coil are different from each other.

6. The coil unit of claim 2, wherein,
the apparatus for detecting foreign matter further comprises a plurality of detecting coils,
each of the plurality of detecting coils is disposed so as to be magnetically coupled to each resonator of the plurality of resonators.

7. The coil unit of claim 3, wherein,
the apparatus for detecting foreign matter further comprises a plurality of detecting coils,
each of the plurality of detecting coils is disposed so as to be magnetically coupled to each resonator of the plurality of resonators.

\* \* \* \* \*